(12) United States Patent
Bagnasco et al.

(10) Patent No.: US 8,182,483 B2
(45) Date of Patent: May 22, 2012

(54) ORTHOPAEDIC DEVICE TO BE ASSOCIATED WITH THE OUTSIDE OF A BONE

(75) Inventors: Mara Bagnasco, Milan (IT); Daniele Venturini, Povegliano Veronese (IT); Graziano Marini, Castel d, Azzano (IT)

(73) Assignee: Orthofix S.R.L., Bussolengo VR (IT)

( * ) Notice: Subject to any disclaimer, the term of this patent is extended or adjusted under 35 U.S.C. 154(b) by 265 days.

(21) Appl. No.: 12/676,648

(22) PCT Filed: Sep. 8, 2009

(86) PCT No.: PCT/IB2009/006785
§ 371 (c)(1),
(2), (4) Date: Mar. 5, 2010

(87) PCT Pub. No.: WO2010/029406
PCT Pub. Date: Mar. 18, 2010

(65) Prior Publication Data
US 2010/0222778 A1    Sep. 2, 2010

(30) Foreign Application Priority Data
Sep. 11, 2008    (IT) .............................. BO2008A0548

(51) Int. Cl.
*A61B 17/00*    (2006.01)
(52) U.S. Cl. ........................................... 606/58; 606/59
(58) Field of Classification Search .................... 606/54, 606/57–59
See application file for complete search history.

(56) References Cited

U.S. PATENT DOCUMENTS

| | | | |
|---|---|---|---|
| 4,135,505 A * | 1/1979 | Day ............................... | 606/59 |
| 4,312,336 A | 1/1982 | Danieletto et al. | |
| 4,988,349 A | 1/1991 | Pennig et al. | |
| 5,019,077 A * | 5/1991 | De Bastiani et al. ........... | 606/54 |
| 5,207,676 A | 5/1993 | Canadell et al. | |
| 5,429,637 A * | 7/1995 | Hardy .............................. | 606/54 |
| 5,743,898 A * | 4/1998 | Bailey et al. .................... | 606/54 |
| 5,788,695 A | 8/1998 | Richardson | |
| 5,951,556 A * | 9/1999 | Faccioli et al. ................. | 606/65 |
| 6,235,029 B1 * | 5/2001 | Faccioli et al. ................. | 606/54 |
| 6,565,564 B2 * | 5/2003 | Hoffman et al. ................ | 606/59 |
| 6,678,562 B1 * | 1/2004 | Tepper et al. ................... | 607/51 |
| 7,041,103 B2 * | 5/2006 | Hoffmann-Clair et al. ..... | 606/59 |
| 7,588,571 B2 * | 9/2009 | Olsen .............................. | 606/57 |

FOREIGN PATENT DOCUMENTS
FR    2 705 881 A    12/1994

* cited by examiner

*Primary Examiner* — Eduardo C Robert
*Assistant Examiner* — Ellen C Hammond
(74) *Attorney, Agent, or Firm* — Husch Blackwell LLP

(57) ABSTRACT

The present invention regards an orthopedic device to be associated with the outside of a bone and of the type comprising a support rail, extended along a central longitudinal axis substantially parallel to the bone, at least two clamps mounted slidably along the axis on the support rail and supporting endosseous screws insertable into the bone, and a distractor/compressor device removably attachable to the two clamps by means of respective connection pins inserted into corresponding holes of each clamp, wherein each clamp comprises a clamp body having a base or lower jaw and a lid, or upper jaw as well as two screws for fixing the upper jaw to the lower jaw Advantageously the holes for the connection pins are aligned along a line that is extended substantially parallel to the axis with at least one hole for the connection pins of the remaining clamp also being aligned along the line, thus making the overall structure of the clamps mounted on the orthopedic device particularly compact.

15 Claims, 8 Drawing Sheets

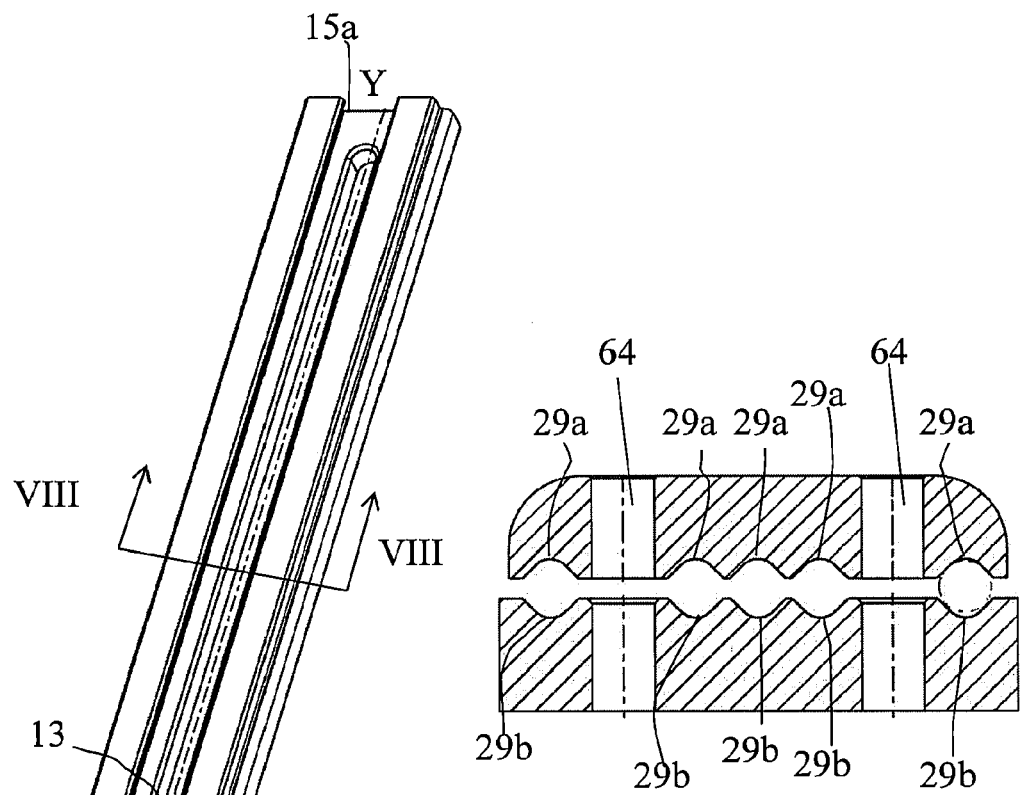
Fig. 6
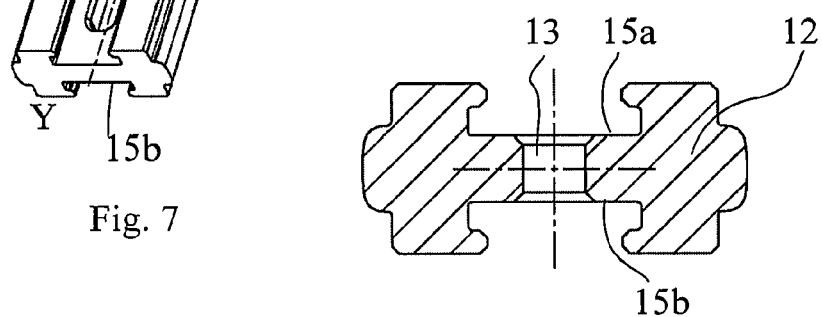
Fig. 7
Fig. 8

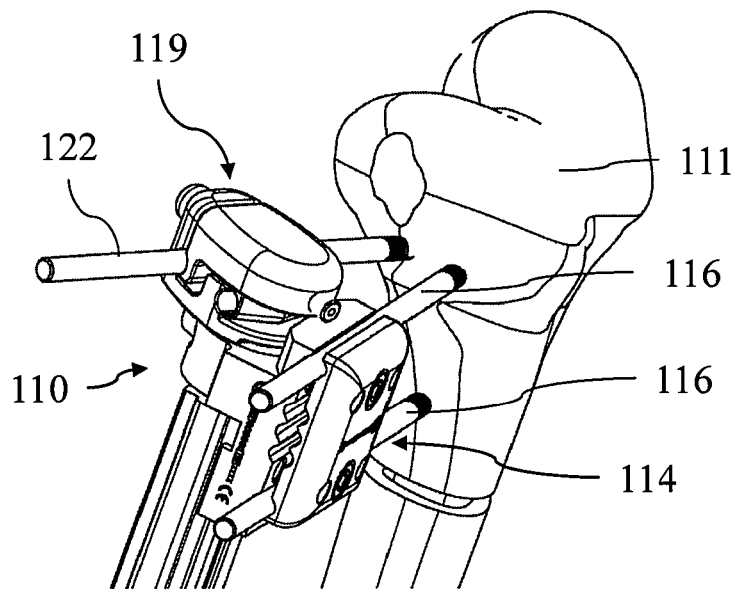
Fig. 9A
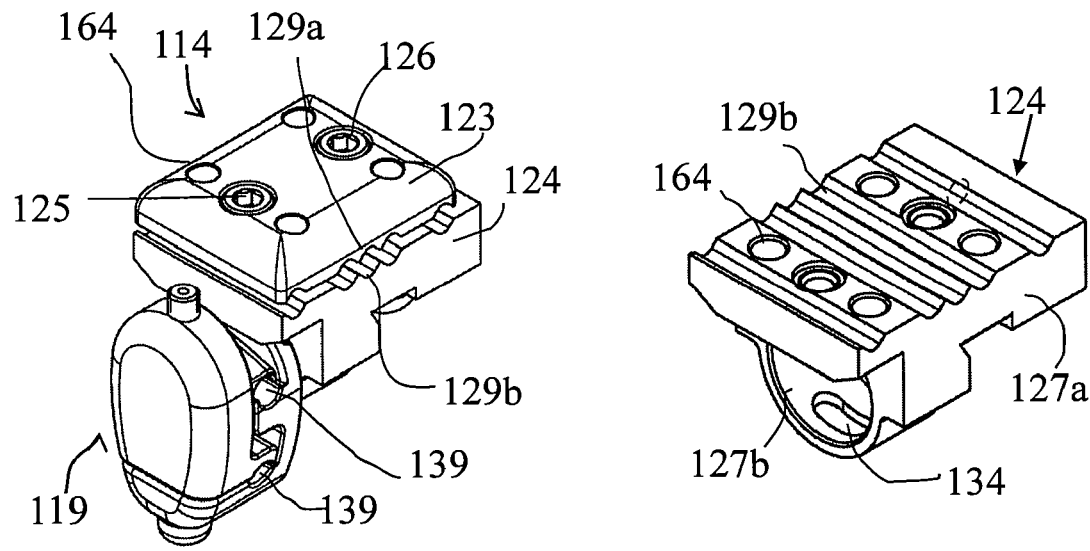
Fig. 10
Fig. 11

ORTHOPAEDIC DEVICE TO BE ASSOCIATED WITH THE OUTSIDE OF A BONE

FIELD OF APPLICATION

The present invention refers in its most general aspect to the field of orthopaedics, in particular to an orthopaedic device to be associated with the outside of a bone, such as, for example, an external fixator for the ostheosynthesis of a bone fracture, or an orthopaedic device for correcting bone deformation or malformation, or for the reconstruction of defective bone. Such an orthopaedic device is of the type comprising one or two clamps mounted on a support rail that are moved in an incremental manner reciprocally nearer to or further away from each other by means of a compressor/distractor device.

Even more particularly the present invention concerns a clamp for the support of endosseous screws that is slidably mounted on said orthopaedic device.

For the sake of brevity and simplicity the following description refers specifically to an orthopaedic device and to the related clamps for the correction of deformations in long bones, but it is intended that this may, by analogy, also be extended to any external orthopaedic device with at least two clamps mounted on a support rail, themselves connected by means of the compressor/distractor device.

PRIOR ART

In orthopaedics the use of orthopaedic devices that are associated with the external part of a bone and equipped with clamps to support endosseous screws that can be inserted into long bones transversely, is well known, for instance for the correction of a deformation of the bone, or for the osteosynthesis of a fracture.

Normally such orthopaedic devices contain two clamps located at a set distance from each other on a support rail. Each clamp usually contains a lower jaw and an upper jaw, closed onto each other, with transverse grooves for guiding the endosseous screws.

More particularly a first clamp is placed in correspondence with a proximal part of the bone in order to insert the first endosseous screws in that position, and the other clamp is placed in a corresponding distal position of the bone in order to insert the second endosseous screws in that position.

When the orthopaedic device is used for the correction of deformed long bones, the correction is usually carried out by subjecting the bone to osteotomy between the distal and the proximal portion and maintaining contact between the two bone extremities through the endosseous screws. Successively the two clamps are moved at incremental steps along the support rail with the help of a distractor/compressor device so that step by step bone callus is generated between the extremities.

More particularly the distractor/compressor device is formed by an operator screw that is connected to the clamps by means of respective connection pins that are inserted into corresponding holes or cylindrical cavities in the body of each clamp. By rotating the screw it is then possible to obtain a relative displacement of the two clamps and as a result a movement further apart or closer together of the positions of the extremities of the bones attached to them.

Such an orthopaedic device, even though it has many advantageous aspects and although it basically obtains the goal for which it is intended, nevertheless presents known inconveniences that have not yet been overcome.

The main inconvenience of such orthopaedic devices is due to the fact that the clamps take up a great deal of space due to their overall size, because of the necessity of having to accommodate within each clamp's body a plurality of components and functional elements, such as the guiding grooves for the endosseous screws, the endosseous screws themselves, the holes for receiving the connection pins of the compressor, the clamping screws of the two jaws, as well as means for blocking the jaws on the support rail. To sum up, a plurality of fastening means has to coexist in the body of each clamp.

The large dimensions of the clamps consequently bear down heavily on the overall weight and dimensions of the orthopaedic device, as well as on the maximum number of clamps that can be placed on a support rail, within a determined weight.

The technical problem at the basis of the present invention is that of devising a clamp and an orthopaedic device including such a clamp, with such structural and functional characteristics that the abovementioned inconveniences in view of the prior art are overcome, and in particular a device that may use a clamp with dimensions that are smaller than those of the clamps of the prior art but with support for an equal number of endosseous screws.

SUMMARY OF THE INVENTION

The technical problem is resolved by an orthopaedic device of the type described previously and comprising a support rail, extending along a central longitudinal axis substantially parallel to the bone, at least two clamps mounted slidably along said axis on the support rail and supporting endosseous screws that can be inserted into the bone, and a distractor/compressor device that can be removably coupled with the two clamps by means of respective connection pins inserted into corresponding holes on each clamp, wherein each clamp comprises a clamp body with a base or lower jaw, and a lid or upper jaw, as well as a screw for fixing the upper jaw to the lower jaw, characterised by the fact that at least one of said two clamps comprises two holes for the connection pins that are aligned on a line that is extended substantially parallel to said axis, with at least one hole for the connection pins of the remaining clamp also being aligned along said line.

Advantageously the device according to the invention distinguishes itself also by the fact that the support rail has a double T-profile, and two opposed grooves where in the centre of each groove a longitudinal slot is extended; the clamping screws of the clamps being arranged along the axis of the support rail.

Moreover, each T-portion of the rail has a wing with end segments bent into an L-shape, so that the two grooves also have a substantially T-shaped form, intended to receive by insertion a conjugate T-shaped projection of the lower jaw of each clamp.

Furthermore, there are four holes for the connection pins, arranged two by two along respective lines that extend substantially parallel equidistant on either side of the central longitudinal axis of the support rail.

The invention also regards the distinguishing characteristics of a group of clamps in accordance with claims 5 to 15. Further characteristics and advantages of the orthopaedic device and the group of clamps according to the invention will become clear from the following description of a number of embodiments, provided by way of non-restrictive example and with reference to the enclosed drawings.

BRIEF DESCRIPTION OF THE DRAWINGS

FIG. 6 is a cross-section view along the line VI-VI of FIG. 4;

FIG. 7 is a perspective view of a detail of the orthopaedic device of FIG. 1;

FIG. 8 is a cross-section view along the line VIII-VIII of FIG. 7;

FIGS. 9 and 9A respectively are perspective views of a second embodiment of an orthopaedic device according to the invention, seen from two different angles;

FIG. 10 is a perspective view of a clamp of the orthopaedic device of FIG. 9;

FIG. 11 is a view of a detail of the clamp of FIG. 10;

DETAILED DESCRIPTION

With reference to the Figures, the reference numbers 10, 110 indicate two different embodiments of an orthopaedic device to be associated with the exterior of a bone, such as for example an external fixator for the osteosynthesis of a fractured bone, or an orthopaedic device for correction of deformed or malformed bones, or for the reconstruction of defective bones. Such an orthopaedic device 10, 110 is of the type comprising two or more clamps mounted on a support rail, and moveable in an incremental manner nearer to or further away from each other by means of a compressor/distractor device.

Figure 1:
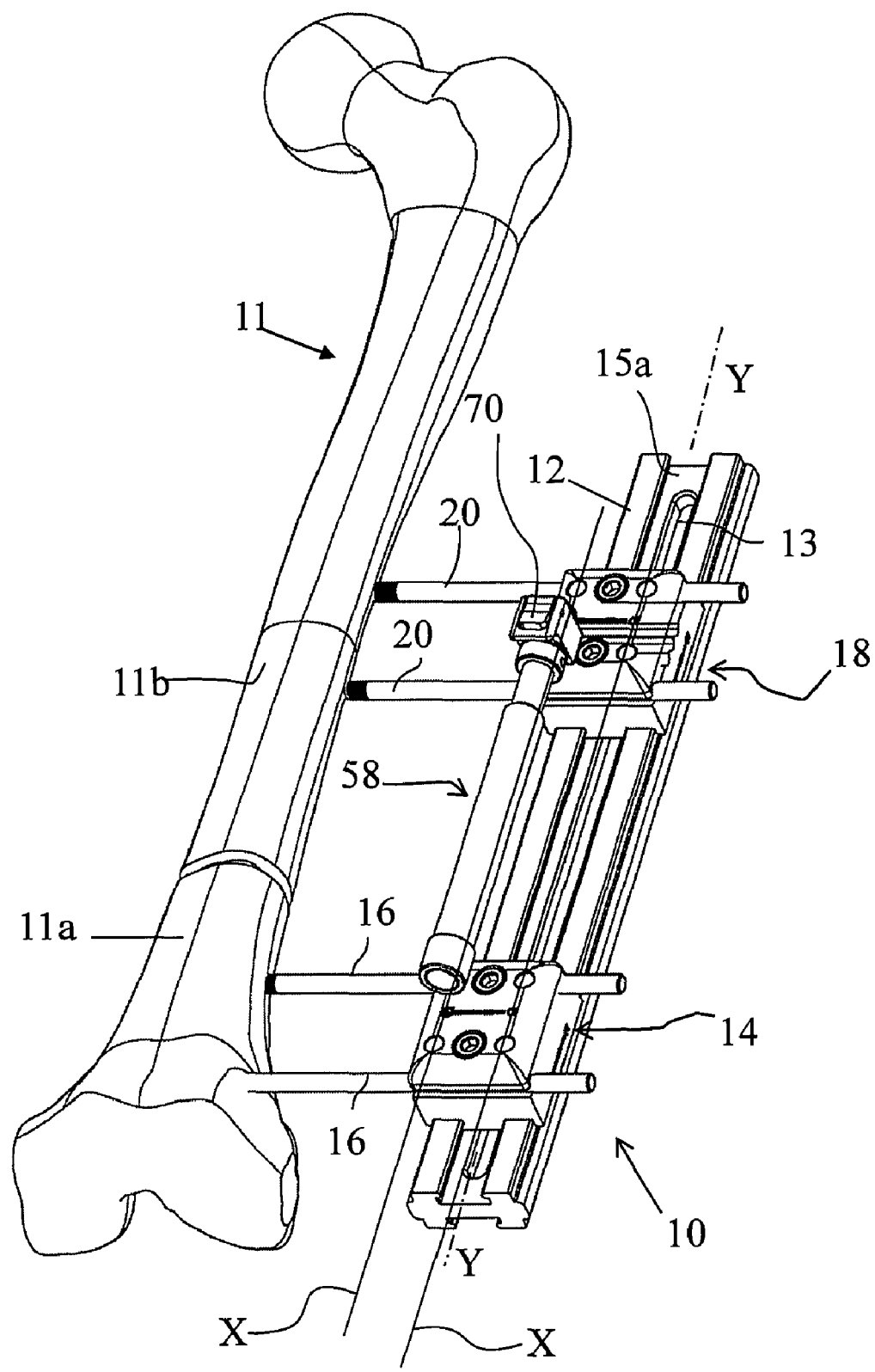
FIG. 1 is a perspective view of a first embodiment of an orthopaedic device according to the invention.
Figure 1A:
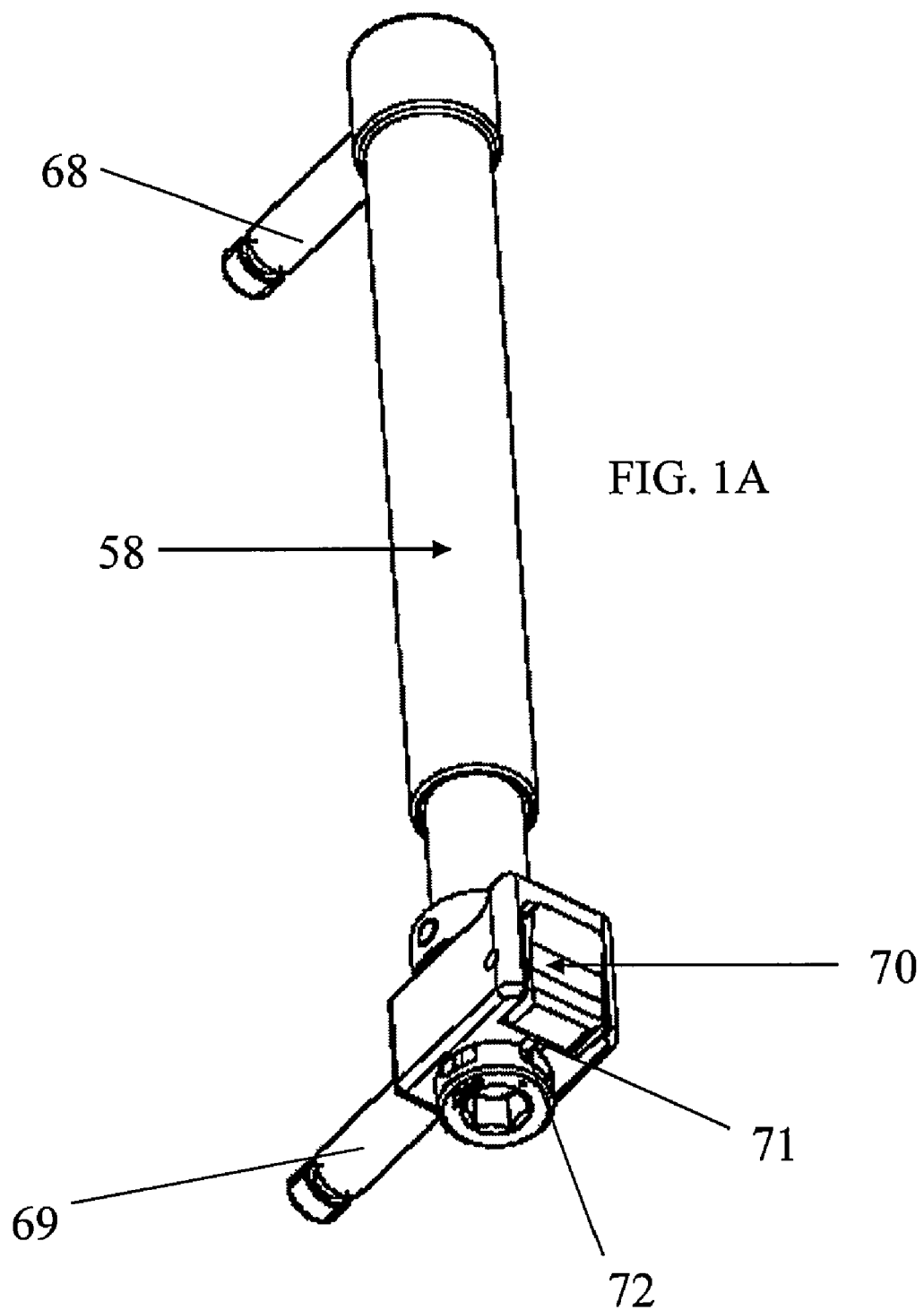
FIG. 1A shows a perspective view of a detail of the orthopaedic device of FIG. 1.
Figure 9:
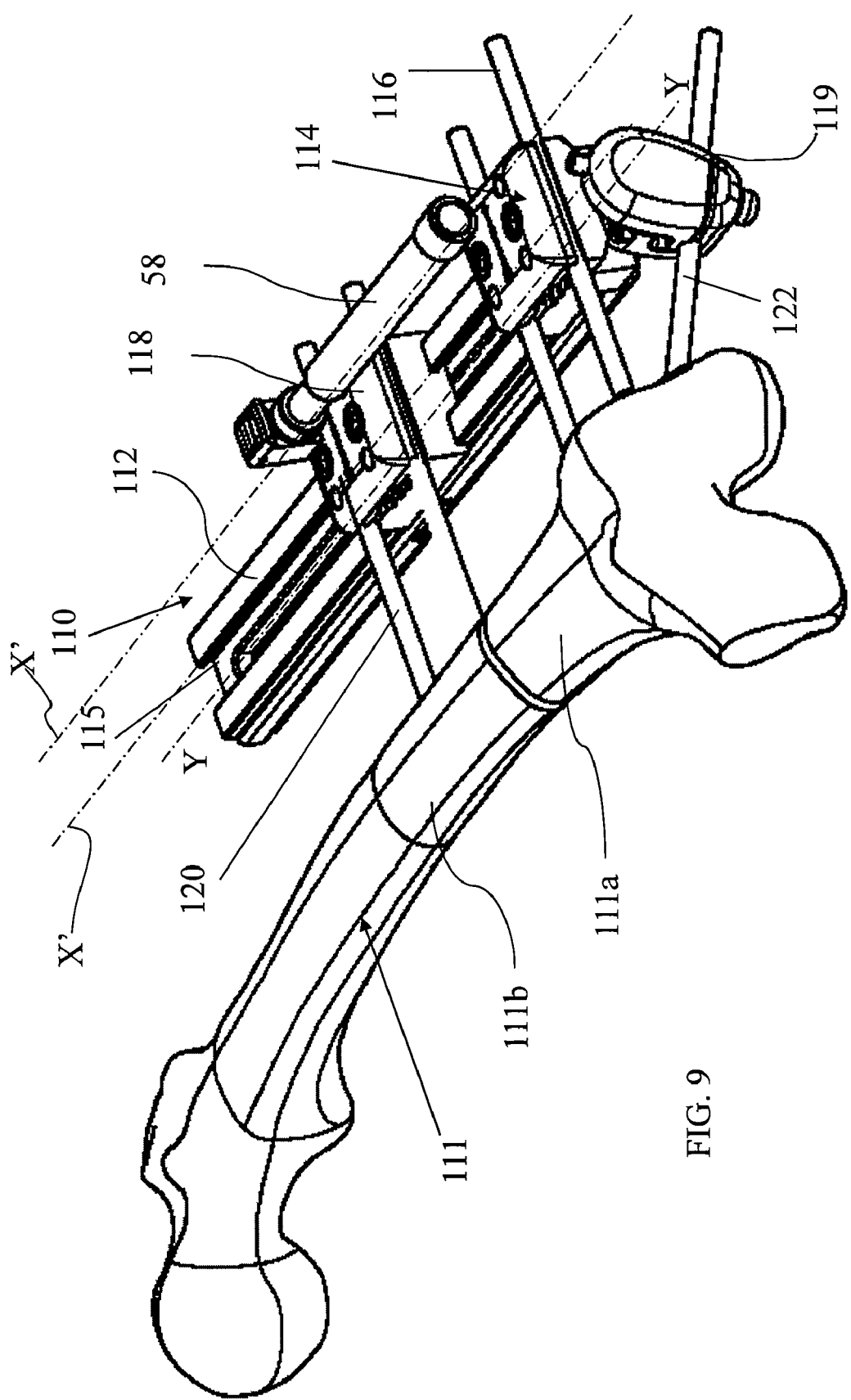
Figure 12:
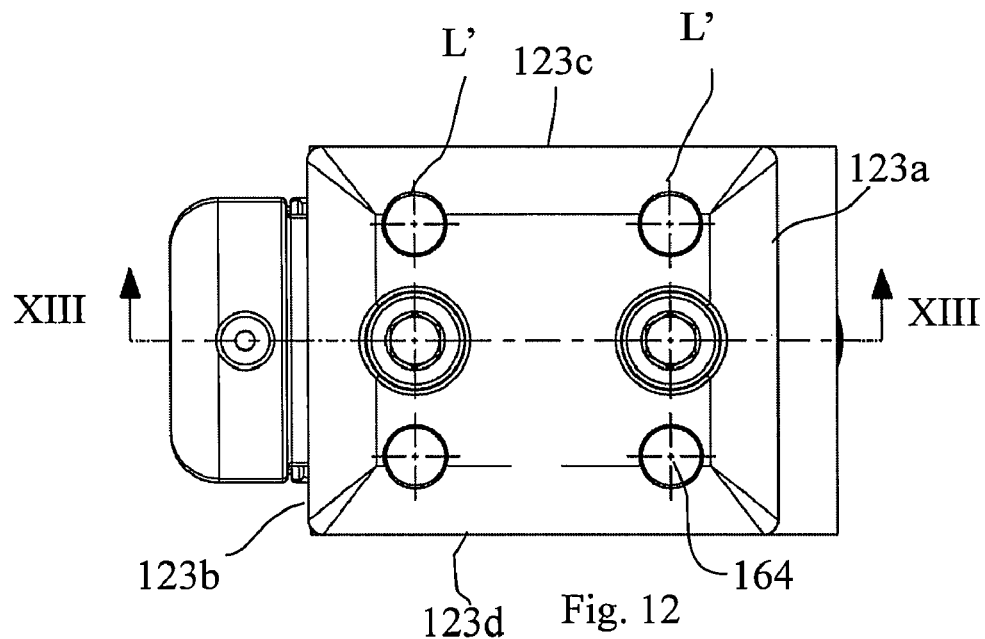
FIG. 12 is a plan view of the clamp of FIG. 10.

In the example of FIG. 1, the orthopaedic device 10 is intended to correct deformations in a long bone 11 such as a tibia or a femur, in correspondence to a substantially central zone of the bone, whereas the orthopaedic device 110 of FIG. 9 is intended to correct deformations in relation to the metaphysis of a femur 111 or of a tibia.

More particularly, as the relative figures mentioned above illustrate, in order to allow for the correction of the deformation, the bone 11 has preemptively been subjected to osteotomy with the formation of two extremities 11a, 11b.

The orthopaedic device 10 contains a rail 12, which in the example is made of a fibre-reinforced thermoplastic material, such as the material commercially known as Orthtek WF®, carbon fibre in epoxy resin pultrusion, or known commercially as Peek CA30®, or in an aluminium alloy. The rail 12 is extended longitudinally along a determined central axis Y-Y, placed laterally and substantially parallel to the bone 11.

In the example, as can be seen in FIGS. 7 and 8, the rail 12 has a double-T profile, and comprises two opposed grooves 15a, 15b. Even more particularly, as shown in FIG. 8, each T-shaped portion of the rail 12 has wings with the end segments bent into an L-shape so that also the two grooves 15a, 15b have a substantially T-shaped form. In the centre of each of the grooves 15a, 15b there is a longitudinal slot 13.

The device 10 moreover comprises at least a first clamp 14 that supports a first group of two endosseous screws 16 inserted into the first bone extremity 11a, and a second clamp 18 that supports a second group of endosseous screws 20 inserted into the second bone extremity 11b. Both clamps are made of fibre-reinforced thermoplastic material, such as the material commercially known as Peek CA30®, or in an aluminium alloy. The endosseous screws 16, 20 are made of implantable steel or titanium alloy.

In the example the two clamps 14, 18 are mounted directly on the rail 12, in a removable manner, and they are identical.

Each clamp 14, 18, as illustrated with reference to the clamp 18 in FIGS. 3, 4, 5 and 6, comprises a clamp body with an upper jaw 23, which forms the removable lid of the clamp, and a lower jaw 24, which forms the fixed base of the clamp, which close onto each other by means of two clamping screws 25, 26, made in the example of steel and/or titanium alloy.

Both jaws 23 and 24 have a substantially rectangular shape, with the respective shorter sides 23a, 23b, 24a 24b of a relatively limited length, around 40 mm in the example, and the respective longer sides 23c, 23d, 24c, 24d of a length relatively limited of around 48 mm in the example. Basically, in the example, the body of the clamp has a maximum overall length not exceeding 50 mm.

More particularly the lower jaw 24 has a transverse profile of a substantially "T"-shaped form with the vertical tail 27 also having a profile in the shape of an upside-down T, which is slidably inserted into the conjugate groove 15a of the rail 12. The lower jaw 24 is fastened in a specific longitudinal position on the rail 12 by means of a blocking screw 28 inserted into the longitudinal slot 13.

Moreover each jaw 23, 24 comprises respective transversal guiding grooves 29a, 29b, defining seats 29 for guiding, and housing the endosseous screws 16, 20. In the example the guiding grooves 29a, 29b have a profile that is substantially V-shaped to receive endosseous screws of different diameters; also in the example the grooves have an angular width of 90°, and receive screws with a diameter of 5 or 6 mm.

The first clamp 14 and the second clamp 18 are connected by means of a compressor/distractor device 58, which allows for the displacement, in an incremental manner, relatively nearer to or further away from each other, of the two clamps 14, 18 and therefore also of the two extremities 11a, 11b. The compressor/distractor 58 is connected to the clamps by means of connection pins 68 and 69 that are inserted with pressure into the corresponding holes 64, or hollows, with a cylindrical form and internally smooth, in the clamps 14, 18.

In the present invention at least one of the two clamps 14 or 18 comprises two holes 64 for the insertion of one of the two connection pins 68, 69 of the compressor/distractor 58, the remaining connection pin being inserted into a further hollow located on the other clamp 18 or 14. The two holes of the first clamp and the remaining hole of the second clamp are aligned along a line X that extends substantially parallel to the central longitudinal axis Y-Y of the rail 12.

In the preferred embodiment each clamp 14, 18 has four holes for the connection pins, aligned two by two along respective lines X that extend substantially parallel to the central longitudinal axis Y-Y of the rail, placed equidistant from this axis Y-Y.

According to one aspect of the invention the holes 64 for the insertion of the connection pins 68 and 69 are placed next to each other and aligned with the clamping screws 25, 26 of the respective clamps 14, 18, along a line L that is substantially parallel to the guiding grooves 29a, 29b, transversal with respect to the central axis Y-Y of the rail, in effect, in the example, forming a right angle with the Y-Y axis of the rail.

Each clamp 14, 18 comprises four holes 64. In particular, each clamp 14, 18 comprises two holes 64 aligned on opposite sides with respect to the first clamping screw 25, and two holes 64 aligned and on opposite sides with respect to the second clamping screw 26. There are, therefore, two alignments or rows, each including two holes 64 and a screw 25, 26 at the centre.

According to another aspect of the invention the holes 64 extend in depth both into the upper jaw 23 and into the lower jaw 24 of each clamp 14, 18. Basically each pin 68 of the compressor/distractor 58 is inserted deeply into the body of each clamp.

Figure 2:
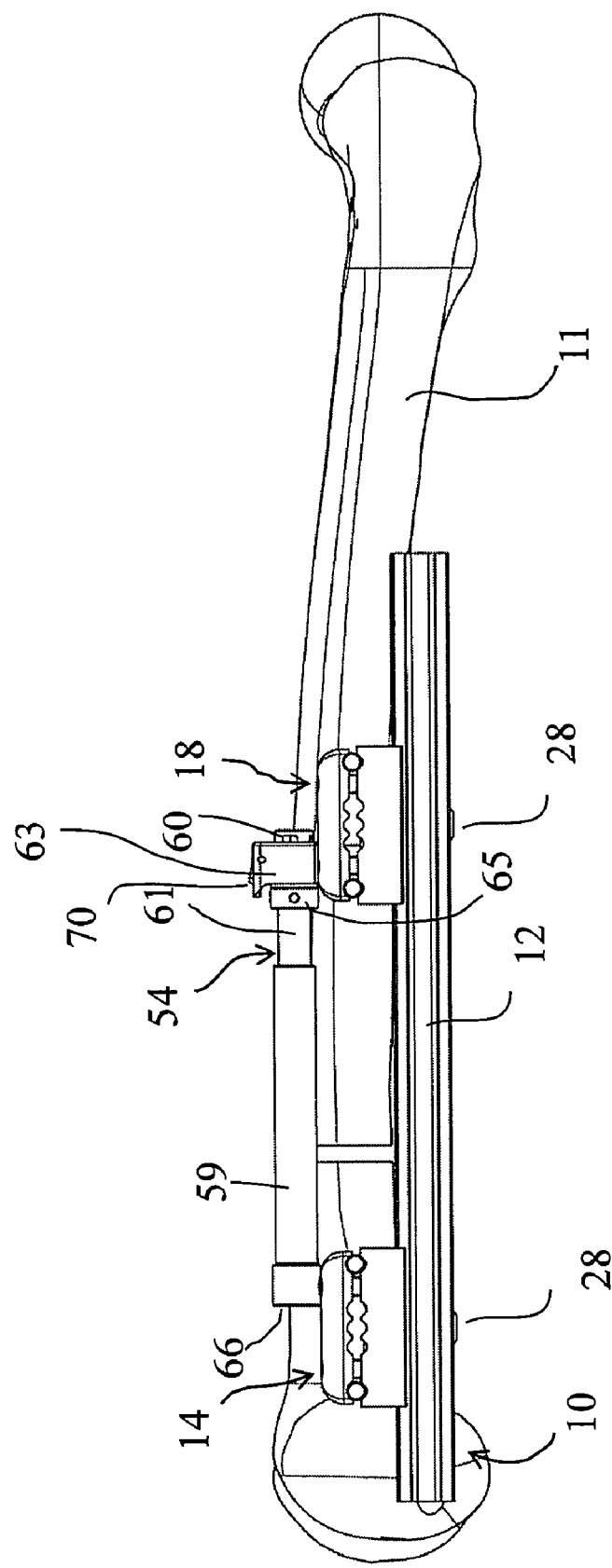
FIG. 2 is a side view of the device of FIG. 1.
Figure 3:
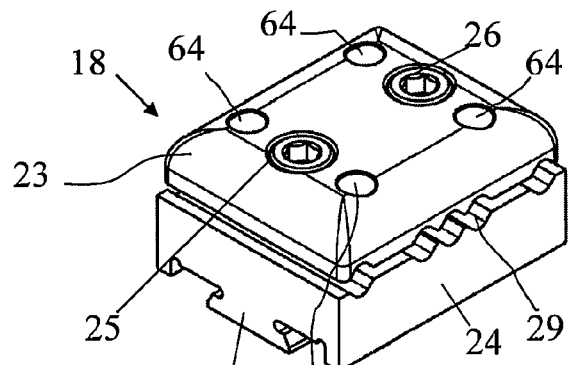
FIG. 3 is a perspective view of a clamp according to the invention associated with the orthopaedic device of FIG. 1.
Figure 4:
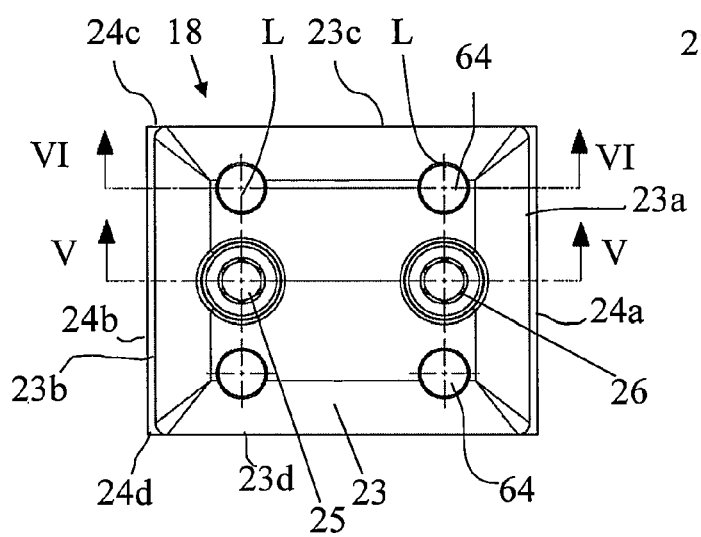
FIG. 4 is a plan view of the clamp of FIG. 3.
Figure 5:
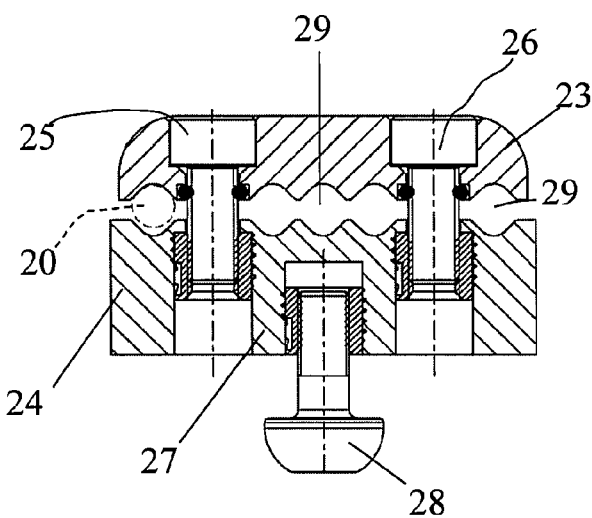
FIG. 5 is a cross-section view along the lines V-V of FIG. 4.

Consequently it follows that for reasons of size, the holes 64 and the screws 25, 26 of the respective clamp 14, 18 are located in parts of the clamp 14, 18 that are not occupied by the guiding grooves 29a, 29b. As is clearly illustrated by the side view of FIG. 2 and the cross sections of FIGS. 5 and 6, along the transverse section parallel to the long side 23c, 23d, 24c, 24d of the clamp 14, 18, the grooves 29a, 29b, and the two lines L or rows of screws 25, 26 and holes 64 alternate.

According to another aspect of the invention each clamp 14, 18 contains five transverse seats 29 for osseous screws, distributed as follows: one central group of three seats 29 for osseous screws, and two lateral seats 29, each in correspondence with a lateral zone or side of the relative clamp 14, 18, substantially in correspondence with the edge of the short side 23a, 23b, 24a, 24b. In this configuration each row of screws 25, 26 and holes 64 is located next to a central group of seats 29, between the latter and a respective lateral seat 29.

Moreover it is possible to observe how in all clamps the four holes 64 described above are placed at the corners of a rectangle, in proximity to the four corners of the relative clamp 14, 18.

This configuration allows for more possible choices for the position of the insertion of a respective pin 68 of the compressor/distractor 58.

In the illustrated solution the compressor/distractor 58 comprises a sleeve 59 that is threaded internally, in correspondence to a portion of the extremity 66 from which a first pin 68 is affixed, a cylindrical shaft 63 to which a second pin 69 is attached, and an operator screw 54 with head 60, housed in the cylindrical shaft 63 and provided with a countersunk hexagon and stem 61 whose external threading matches the internal threading of the sleeve 59. The compressor/distractor 58 moreover contains an annular body 65 solidly in rotation with the stem 61 of the screw, and placed near the cylindrical shaft 63, functioning as an axial stop 12.

Once the connection pins 68 and 69 have been inserted into the corresponding holes 64 of the clamps 14, 18 it is sufficient to rotate the screw by inserting a key into the countersunk hexagon of the head 60 to obtain a relative displacement of the two clamps 14 and 18 along the rail 12, and as a result a displacement, nearer to or further away from each other, of the positions of the bone extremities connected to them.

To allow a user to safely control the relative displacement of the clamps 14, 18 the compressor 58 comprises a button element 70, provided on the edge of a prominence 71 that is inserted into a corresponding notch 72 present on the external surface of the head 60.

In particular the head 60 of the screw has four notches, staggered at 90°. In order to operate the screw 54, the button element 70 is pushed in order to disengage the prominence 71 from the notch 72. The screw is then made to rotate until it engages, by means of pressure on the button element 70, the prominence 71 of the next notch or the one after that. This allows a user to know that a quarter turn or a half turn of the screw 54 has been completed, which in the example corresponds to a reciprocal displacement of the clamps of 0.25 mm or 0.5 mm respectively.

The main advantage of the clamp and the related orthopaedic device according to the present invention, lies in the fact that it possesses a greater number of seats for transverse screws while maintaining generally modest measurements. In fact the clamping screws side by side with the holes for the insertion of the pins of the compressor together occupy a reduced space of the body of the clamp, leaving more room available for the guiding grooves, and thus for the endosseous screws. In this manner the clamp according to the present invention has dimensions that are altogether reduced while at the same time maintaining the same number of guiding grooves as a clamp known from the prior art.

For example, in the illustrated embodiments the clamp has five transverse seats, that allow for ample choice in the reciprocal placement of the two endosseous screws.

A further advantage lies in the fact of the specific distribution of the two rows of holes, alternating between a central group of at least three guiding grooves, and two lateral guiding grooves. This disposition allows for further greater possibilities in the choice of position of the two endosseous screws, e.g. both in the central group, or one in the central group and one in a lateral groove, etc . . . .

Yet another further advantage lies in the fact that the clamp has four holes for the insertion of the pins, which creates a sufficiently wide margin of freedom in the choice of the most useful arrangement of the compressor/distractor with respect to the clamps and the rail, when the orthopaedic device is mounted next to the bone.

A further advantage of the clamp according to the present invention lies in the fact that it is possible to insert the pins of the compressor/distractor deeply into both jaws, which guarantees great stability in the connection with the relative clamps.

Now, with particular reference to the FIGS. 9-13 a second embodiment of an orthopaedic device according to the present invention will be illustrated.

The orthopaedic device 110 contains at least a first clamp 114, and a second clamp 118, both mounted on a rail 112 which has the same structure and function as the rail 12 previously described.

More particularly the second clamp 118 is the same as the clamp 14, or 18 of the previously described embodiment, supporting a group of endosseous screws 120 inserted in the proximal extremity 111b of a bone 111, whereas clamp 114 constitutes the main clamp of a group of clamps mounted on the rail 112 at one of its extremities, and that support endosseous screws 116, 122 inserted into a metaphyseal region of the bone 111 (distal bone extremity 111a).

In particular the group of clamps contains, in addition to the main clamp 114, an auxiliary clamp 119 that is located on the main clamp 114 and that supports the respective endosseous screws 122.

The auxiliary clamp 119 is placed on the main clamp 114 in such a manner that the respective endosseous screws 116 and 122 are located on planes P and P', together substantially forming a right angle.

In particular the main clamp 114 contains an upper jaw 123, which constitutes the removable lid of the clamp, and a lower jaw 124, forming the base of the clamp, closed between them by means of two clamping screws 125, 126.

The upper jaw 123 has a substantially rectangular shape, similar to the upper jaw in the previously described embodiment, with short sides 123a, 123b of 40 mm and long sides 123c, 123d of 48 mm.

The lower jaw 124, just as in the previously described embodiment, contains a central body 127a, substantially having the shape of a rectangular plate of relatively small dimensions, in the example 53.7 mm×40 mm, with a vertical tail 131 that protrudes from the central body 127a and that is slidably inserted into a groove 115 of rail 112 that has the shape of an upside-down T, fixed in a specific longitudinal position by means of a blocking screw 133.

Each jaw 123, 124 moreover contains transverse guiding grooves 129a, 129b respectively defining seats 129 for guiding and housing the endosseous screws 116.

The main clamp 114 and the clamp 118 are connected by means of a compressor/distractor device 58, which allows for the incremental displacement, either closer to or further away from each other, of the two clamps 114, 118, and therefore of the two bone extremities 111a, 111b. The compressor/distractor 58 is connected to the clamps by means of connection pins 68 of the type previously described, inserted by means of pressure into the corresponding holes 164, or hollows, of a cylindrical shape and internally smooth, in the clamps 114, 118.

According to the present invention at least one of the two clamps 114 or 118 contains two holes 164 for the insertion of one of the two connection pins 68, 69 of the compressor/distractor 58, the remaining connection pin being inserted into a further hole in the other clamp 118 or 114. The two holes of the first clamp and the remaining hole of the second clamp are aligned along a line X' that extends substantially parallel to the central longitudinal axis Y-Y of the rail 112.

In its preferred embodiment each clamp 114, 118 presents four holes for the connection pins, aligned two by two along respective lines X' that extend substantially parallel to the central longitudinal axis Y-Y of the rail, placed equidistant from said axis Y-Y.

According to an aspect of the invention the holes 164 for the insertion of the connection pins 68 of the compressor/distractor are placed alongside each other and aligned with the clamping screws 125, 126 of the clamp 114, along a line L' substantially parallel to the guiding grooves 129a, 129b, transverse with respect to an axis Y-Y of the rail 112.

In the example the clamp 114 comprises four holes 164. In particular each clamp 114 contains two holes 164 aligned, on opposite sides, with the first clamping screw 125, and two holes 164 aligned, on opposite sides, with the second clamping screw 126. There are, therefore, two alignments or rows, each including two holes 164 and a screw.

Also in this embodiment the holes 164 extend in depth through the upper jaw 123 and into the lower jaw 124. Moreover, also in this embodiment all along the transverse section parallel to the long side of the clamp 114 there are alternating grooves 129a, 129b and two rows of screws 125, 126 and holes 164; in particular one may note a group of three seats 129 in the centre, and a seat 129 on each side of the clamp 114.

Figure 13:
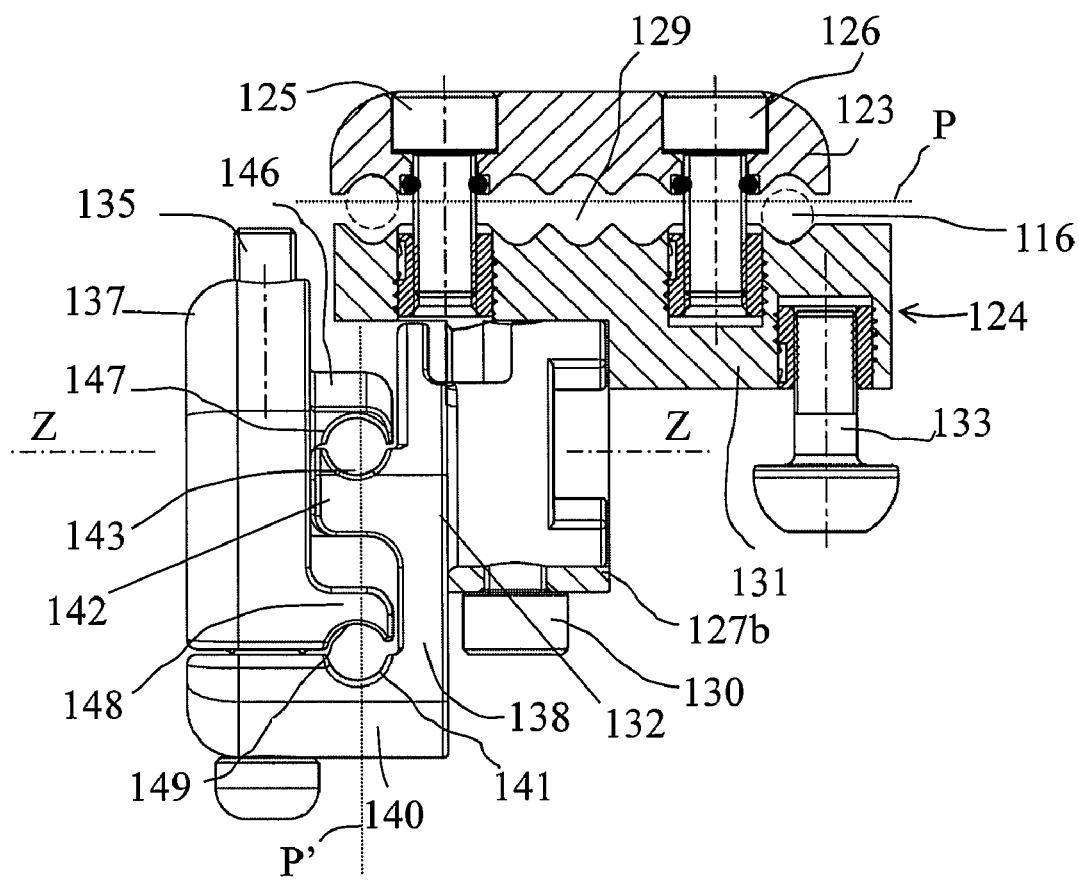
FIG. 13 is a cross-section along the line XIII-XIII of the clamp of FIG. 12.

The lower jaw 124 moreover comprises, next to the vertical tail 131, a substantially cylindrical collar-shaped appendix 127b, of axis Z-Z, protruding from the central body 127a and intended to receive a corresponding cylindrical appendix 132 of the auxiliary clamp 119, partially visible in FIG. 13, which is blocked by means of a screw 130. The cylindrical collar 127b is provided with a slot 134 in which the screw 130 is accommodated, wherein this slot 134 extends on the cylindrical surface on an arc of a circle which subtends an angle of about 35° with the centre on the axis Z-Z. The connection between the appendix 132 and the cylindrical collar 127b allows for the angular movement on the plate P' of the auxiliary clamp 119, obtaining a regulation of the angular position of the two clamps 114 and 119.

The auxiliary clamp 119 in turn comprises a lower jaw 138 with is made of one piece with the abovementioned connection appendix 132, and an upper jaw 137, which are closed by means of a screw 135.

The endosseous screws 122 are housed in transverse seats 139 between the two jaws 137 and 138; these seats are created by counterposed concavities or guiding grooves.

In particular the lower jaw 138 has a lateral edge 140 provided on the side of a first guiding groove 141 which is placed in proximity to an end projection 148 of the upper jaw 137 provided with an opposite guiding groove 149.

The lower jaw 138 moreover comprises a central prominence 142 on the side of a guiding groove 143 which is placed in proximity to a prominence 146 of the upper jaw 137, provided on the side of a counterposed guiding groove 147.

As can be observed in the Figures, the locking screw 135 passes through the edge 140, the projection 148 and the prominences 142, 146 parallel to the plane P'. Thanks to this arrangement it is possible, by rotating the locking screw 135, to regulate the relative position of the two jaws on the plane P', which allows for the adjustment according to necessity of the dimension of the transverse seats 139 for the endosseous screws 122 accommodated therein, to accommodate screws or other tubular fixation elements with different dimensions, without modifying the reciprocal distance between these.

The main advantage of the main clamp in the latter embodiment lies in the fact that, as in the previous embodiment, it presents a greater number of seats for the transverse screws, with dimensions that are generally modest. In effect the clamping screws and the holes for the insertion of the connection pins of the compressor, being placed side by side in a line, occupy less space on the body of the clamp, which leaves more space for the guiding grooves. In this manner the clamp according to the present invention has dimensions that are altogether reduced while at the same time maintaining the same number of guiding grooves as a clamp known from the prior art.

Also the main clamp of this second embodiment has five transverse seats, which offer more possibilities in the choice of positioning of the two endosseous screws, wherein said seats are preferably distributed with a central group of at least three seats, and two lateral seats.

A further advantage of the orthopaedic device in accordance with this second embodiment lies in the fact that it is possible to adjust not only the position of the endosseous screws on the main clamp, but also to adjust the position of the endosseous screws supported by the main clamp with respect to the endosseous screws supported by the auxiliary clamp.

Thanks to the possibility of the angular movement of the connection appendix in the cylindrical collar, it is in fact possible to adjust the reciprocal position of the screws on relative planes, to meet the specific anatomical needs of the bone.

A further advantage lies in the possibility, as mentioned above, to vary the dimension of the transverse seats of the auxiliary clamp.

Obviously numerous modifications and variations can be applied to the clamp and the orthopaedic device described above by a person skilled in the art to meet contingent needs and specifications, which are in any case contained within the scope of protection of the invention as defined by the following claims.

The invention claimed is:

1. An orthopedic device for the correction of deformations in long bones to be associated with the outside of a bone, comprising a support rail, adapted to extend along a given central longitudinal axis, at least two clamps mounted slidably along the central longitudinal axis on the support rail and supporting endosseous screws insertable into the bone, and a distractor/compressor device removably attachable to the two clamps by means of respective connection pins inserted into the corresponding holes of each clamp, wherein each clamp comprises a clamp body having a base or lower jaw, and a lid, or upper jaw, as well as two clamping screws for fixing the upper jaw to the lower jaw, at least one of said two clamps comprises two holes to receive one of the connection pins of the distractor/compressor device, the two holes are aligned along a longitudinal line that extends substantially parallel to the central longitudinal axis, and the remaining clamp comprises at least one hole to receive the other connection pin of the distractor compressor device, the at least one hole being aligned with the same longitudinal line.

2. The orthopedic device according to claim 1, wherein each clamp contains four holes for receiving a connection pins that are aligned two by two along respective lines that extend substantially parallel to the central longitudinal axis of the rail and that are equidistant from the rail.

3. The orthopedic device according to claim 1, wherein the support rail has two opposing T-portions forming two opposed clamping grooves extending the entire length of the rail, and wherein a longitudinal slot is placed at the center of each clamping groove forming a single passage for the clamping screws.

4. The orthopedic device according to claim 3, wherein each T-portion of the support rail has a wing with end segments bent into an L-shape so that the two clamping grooves also have a substantially T-shaped form, and are intended to receive by insertion a conjugate T-shaped projection of the lower jaw of each clamp.

5. The orthopedic device according to claim 1, wherein at least one of the clamps bears transversal guiding grooves defining seats for the accommodation of endosseous screws, two of the holes for the connection pin and one of the clamping screws being arranged in alignment with each other along a transversal line which extends substantially in parallel to the guiding grooves and transverse with regard to the central longitudinal axis of the rail.

6. The orthopedic device according to claim 5, wherein each clamp comprises two holes for the connection pin aligned with a first clamping screw, and two other holes aligned with a second clamping screw, defining two rows each including two holes and a clamping screw arranged perpendicular to the central longitudinal axis of the rail.

7. The orthopedic device according to claim 6, wherein each clamp comprises five seats for the accommodation of endosseous screws, distributed as follows: a central group of three central seats and two lateral seats, each of the latter being at a lateral side of the corresponding clamp.

8. The orthopedic device according to claim 7, wherein each of said rows is interposed between the central seats and the respective lateral seat.

9. The orthopedic device according to claim 5, wherein the guiding grooves have a substantially V-shaped profile to receive endosseous screws having different diameters.

10. The orthopedic device according to claim 1, wherein each hole for the connection pin extends in depth through both the lower and upper jaws.

11. The orthopedic device according to claim 1, wherein both the upper and lower jaws have a substantially rectangular shape, with short sides, of a length of about 40 mm, and long sides of a length of about 48 mm.

12. The orthopedic device according to claim 1, wherein it comprises a group of further clamps, to support endosseous screws in the metaphysis of a long bone, comprising at least one main clamp and one auxiliary clamp placed on board the main clamp and supporting respective endosseous screws; the respective endosseous screws of the main clamp and the auxiliary clamp being arranged on planes substantially forming a right angle among themselves.

13. The orthopedic device according to claim 12, wherein the auxiliary clamp is angularly movable in relation to the main clamp, around an axis that is substantially orthogonal to the plane of the endosseous screws of the auxiliary clamp.

14. The orthopedic device according to claim 13, wherein a lower main jaw of the main clamp comprises a substantially cylindrical collar-shaped main appendix, intended to receive a cylindrical auxiliary appendix of the auxiliary clamp, wherein the cylindrical main appendix is provided with a slot in which a main locking screw for the locking of the cylindrical auxiliary appendix is accommodated, wherein such slot extends on a cylindrical surface on an arc of a circle which subtends an angle of about 35° with the center on the axis of the cylindrical main appendix.

15. The orthopedic device according to claim 14, wherein the auxiliary clamp comprises a lower auxiliary jaw, which is made in one piece with the cylindrical auxiliary appendix, and an upper auxiliary jaw, which are closed by means of an auxiliary locking screw arranged substantially in parallel to the plane of the endosseous screws of the auxiliary clamp, wherein said lower and upper auxiliary jaws bear transversal grooves for the accommodation of endosseous screws.

* * * * *